(12) United States Patent
Oultram

(10) Patent No.: US 6,403,340 B1
(45) Date of Patent: Jun. 11, 2002

(54) TEMPLATE CHAIN REACTION

(75) Inventor: John Douglas Oultram, Stretford (GB)

(73) Assignee: Tepnel Medical Limited, Manchester (GB)

( * ) Notice: Subject to any disclaimer, the term of this patent is extended or adjusted under 35 U.S.C. 154(b) by 0 days.

(21) Appl. No.: 09/806,405

(22) PCT Filed: Oct. 20, 1999

(86) PCT No.: PCT/GB99/03457

§ 371 (c)(1),
(2), (4) Date: Mar. 30, 2001

(87) PCT Pub. No.: WO00/23619

PCT Pub. Date: Apr. 27, 2000

(30) Foreign Application Priority Data

Oct. 20, 1998 (GB) ............................................. 9822777

(51) Int. Cl.[7] ........................... C12P 19/34; C12Q 1/68; G01N 33/00; C07H 21/02; C07H 21/04
(52) U.S. Cl. ......................... 435/91.2; 435/6; 435/91.1; 436/94; 536/23.1; 536/24.3; 536/24.33
(58) Field of Search .......................... 435/6, 91.1, 91.2, 435/183; 436/94; 536/23.1, 24.3, 24.33, 25.3

(56) References Cited

U.S. PATENT DOCUMENTS

| 4,683,202 | A | | 7/1987 | Mullis |
| 4,994,368 | A | | 2/1991 | Goodman et al. |
| 5,455,166 | A | | 10/1995 | Walker |
| 5,645,987 | A | | 7/1997 | Richards |
| 5,714,320 | A | | 2/1998 | Kool |
| 5,854,033 | A | | 12/1998 | Lizardi |
| 5,863,732 | A | | 1/1999 | Richards |
| 6,287,824 | B1 | * | 9/2001 | Lizardi ...................... 435/91.2 |
| 6,316,229 | B1 | * | 11/2001 | Lizardi ...................... 435/91.2 |

* cited by examiner

Primary Examiner—Ethan C. Whisenant
Assistant Examiner—Frank Lu
(74) Attorney, Agent, or Firm—Wallenstein & Wagner, Ltd.

(57) ABSTRACT

Methods for synthesizing oligonucleotide products and detecting single-stranded target nucleic acid sequences, are disclosed. The methods include amplifying a template sequence to produce a complementary strand hybridized to the template sequence, which is subsequently cleaved by at least one cleavage agent displacing the complementary strand as a single stranded sequence complementary to the template sequence.

12 Claims, 8 Drawing Sheets

TEMPLATE CHAIN REACTION

The present invention concerns novel methods for detecting single-stranded target nucleic acid sequences.

As used herein the term "nucleic acid" includes protein nucleic acid (i.e. nucleic acids in which the bases are linked by a polypeptide backbone) as well as nucleic acids (e.g. DNA and RNA) having a sugar phosphate backbone, and chemical analogues thereof.

Generally speaking, amplification techniques may be viewed as effecting the detection of a target by amplifying it. However, these typically require a large target sequence since it is to be amplified and must be unambiguously identifiable in order to reduce background noise. These techniques also amplify only the detected sequence, and are unable to provide separate distinct sequences for subsequent detection, for example sequences which will hybridise to other sequences in a detection system, or which are specifically bound by antibodies. For example, amplification techniques used to detect different targets are unable to generate a common product for all of the different targets. Amplification techniques also typically require the use of thermal cycling, thus causing the reaction to pass through many heating and cooling steps. This slows down the reaction, requires the use of expensive thermal cycler devices and of larger quantities of reagents or the use of more expensive thermostable reagents.

One example of an amplification technology is PCR (EP 0201184) in which a pair of complementary template strands are treated with a molar excess of two oligonucleotide primers so that the primers hybridize to the template strands. A polymerase enzyme is then used to extend the primers to produce strands complementary to the template strand sequences. The hybridised templates and complementary strands are then separated by heat denaturation to give two new pairs of complementary template strands. Subsequent cooling allows further primers to hybridise to the template strands. By repeating the cycle of steps, an exponential amplification of the complementary template strands is achieved. A particular disadvantage encountered with PCR is the need to cycle the reaction through many heating and cooling steps, as discussed above.

Isothermal amplification procedures are also known which similarly use a molar excess of primers but avoid the need for thermal cycling by using strand displacing polymerase enzymes (i.e. polymerase enzymes lacking 5' to 3' exonuclease activity), which displace the non-template part of any double stranded DNA they encounter whilst themselves progressing along a template DNA strand to produce double stranded DNA.

Such isothermal amplification techniques are exemplified by the Strand Displacement Amplification of EP 0497272, which provides for amplification of a target nucleic acid sequence, but requires a pair of primers, at least one template strand, and the presence of at least one substituted inter-nucleotide linkages, meaning that amplification products all contain substituted deoxynucleosidetriphosphates. It also requires the use of a second set of primers in reactions.

Rolling Circle Amplification is another isothermal amplification system, requiring a circular single-stranded template. Primers hybridised to the template allow the binding and activity of strand displacing polymerases which circle around the template displacing non-template sequence, and which produce just one single stranded complementary strand containing a number of tandem repeats of the sequence complementary to the template strand. However, the unit copies within the concatamer cannot be manipulated further by processes such as extension against another template unless they have undergone additional further processing. As such they are of extremely limited use when compared to the multiple fixed-length linear products of PCR amplification.

Rolling Circle Amplification can achieve exponential amplification by including a second primer which is complementary to the concatameric strand produced by the first primer. In a cascade reaction the second primer hybridises to the concatameric strand as it is produced and the polymerase enzyme extends it (using the concatamer as template) to generate product. As the linear amplification reaction occurs further sites for hybridisation of the second primer are produced upstream of the extended product. Extension of additional second primer from these sites leads to displacement of the downstream non-template strands which in turn reveal sites for hybridisation of further first primer sequences. Thus occurs a cascade of exponential production of sites and hybridisation thereto and polymerisation of primers therefrom. A disadvantage of this method is the requirement for some pre-treatment of the target (e.g. a ligation of a synthetic nucleic acid, against the target to form a circle) and three synthetic molecules are involved in the most beneficial embodiments of the invention.

The Qβ replicase amplification system relies on the target sequence to anchor a modified version of midivariant 1 (MDV1) to a solid phase, while non-anchored sequences are removed by washing. MDV1 is an RNA molecule which is the specific target for amplification by the RNA-directed RNA polymerase (replicase) of bacteriophage Qβ, producing up to $10^6$ to $10^9$ copies of MDV1 in 15 minutes. An inherent problem with the system is the need for scrupulous washing to remove solution phase copies of MDV1 which are, otherwise, amplified to the same extent as target bound copies, producing a high level of background "noise".

Cycling probe amplification utilises a chemically synthesised probe containing linkages, between some of its nucleotides, which (only when the molecule is rendered double stranded by hybridisation with the target) can be broken by the action of an enzyme. In a typical reaction, the target is denatured with the probe and the reaction is then held at a temperature at which intact probe molecules will hybridise to the target but at which the shorter products of enzymatic degradation will not. Thus, probe molecules hybridise, are cleaved by the enzyme, and the shorter products are displaced by the hybridisation of new probe molecules, in a cyclic reaction. The reaction is essentially linear in nature with the reaction products currently being detected by gel electrophoresis.

U.S. Pat. Nos. 5,645,987 and 5,863,732 (which are incorporated herein by reference in their entirety) disclose the enzymatic synthesis of oligonucleotides using a template strand having a priming region, intervening region and complementary region having a cutting attenuation modification. The priming region is complementary to a desired target oligonucleotide sequence. Upon hybridisation of the target sequence to the priming region, the target sequence is extended by polymerase activity to provide a complementary strand. This results in the production of a double stranded restriction endonuclease recognition sequence which is nicked by the restriction endonuclease, the template strand not being cut because of the effect of the cutting attenuation modification. Additional polymerase activity extends the 3' terminus of the nicked complementary strand 5' to the restriction site, displacing the complementary strand 3' to the cleavage site (i.e. complementary to the complementary region of the template strand) and creating another double-stranded restriction endonuclease recognition sequence. The process can continue ad infinitum to give a linear rate of synthesis of oligonucleotides complimentary to the template strand complimentary region.

A cascade of such reactions can be employed to give non-linear rates of amplification, the displaced complimentary strand from a first reaction acting as a target oligonucleotide complimentary to the priming region of a second template strand, and so on.

WO 92/01813 and Terrance Walker, G. et al. (1992, PNAS USA, 89(1): 392–396; PMID 1309614) disclose methods of circular extension and of amplification.

No suggestion is made as to how to achieve non-linear rates of amplification using a single template strand.

The present invention overcomes the prior art disadvantages and provides new methods for synthesising oligonucleotide products and detecting single-stranded target nucleic acid sequences. Double stranded nucleic acid sequences may of course be detected by separating (melting) them to provide a pair of single stranded sequences and detecting one or both of them using the methods of the present invention.

According to the present invention there is provided a method for synthesising oligonucleotide products comprising the steps of:

(a) providing a circular nucleic acid template sequence having at least one cleavage site which, when rendered double-stranded by a complementary strand, provides a cleavage site for a cleavage agent which cleaves only said complementary strand;

(b) hybridising to said template sequence a target nucleic acid sequence to act as a primer nucleic acid sequence; and (c) treating said template sequence and hybridised primer sequence with a strand-displacing polymerising agent and the reagents and conditions necessary to effect the action of said polymerising agent, and with said cleavage agent or agents; such that said polymerising agent produces a complementary strand hybridised to said template sequence and which is cleaved at said cleavage site or sites, such that it is subsequently displaced as a single-stranded linear nucleic acid by said polymerising agent.

Such a method may be considered a method of amplifying a template sequence to produce single-stranded sequence complementary to it.

Such a method may provide a plurality of displaced (i.e. not even hybridised in part to the template sequence) single-stranded nucleic acid sequences.

Also provided according to the present invention there is a method for detecting the presence of a target nucleic acid sequence, comprising the step of:

(a) performing a method for synthesising oligonucleotide products according to the present invention;

(b) detecting any displaced single stranded complementary strands; and (c) correlating the results of detection step (b) with the presence of said target nucleic acid sequence.

By providing a double-strand specific cleavage site for a cleavage agent and only cleaving the complementary strand, a repeated cycling of a strand-displacing polymerising agent around the circular template produces a series of complementary strand products of equal length.

A number of primers may be hybridised to the circular template strand such that a number of complementary strands are produced in tandem.

It may be desirable to create more than one single-stranded linear nucleic acid complementary strand product from a single circular template, and this may be achieved by providing more than one cleavage site.

Cleavage agents are well known (see below) and different cleavage sites may be cleaved by the same cleavage agent or by different cleavage agents.

A product of the method of the present invention need not include the target nucleic acid sequence and such a product could be the displaced single stranded complementary strand, for example which is detected in step (b) of the detection method.

The primer sequence may hybridise at a position on the template strand which is distant from the cleavage site, or it may hybridise at a position which is near to or which overlaps the cleavage site.

Upon cleavage, a site is presented at the 3' terminus of the complementary strand which may be bound by the polymerising agent and provide a start site for polymerisation. Further cleavage allows a number of polymerising agents to proceed along the template strand at the same time.

The displaced single-stranded linear complementary strand may subsequently hybridise to a single-strand circular template sequence and act as a primer. Thus, if a molar excess of circular template sequences is provided relative to the quantity of primer nucleic acid sequence, exponential amplification of oligonucleotide synthesis may be achieved, only being limited by the quantity of circular template sequences. Such a exponential amplification using a single template sequence to provide a plurality of single stranded nucleic acid products is not suggested by the prior art, which requires e.g. a cascading series of reactions.

The circular nucleic acid may be formed from a linear nucleic acid precursor which may be circularised by any one of a number of methods. For example, the termini of the linear sequence may be hybridised to a complementary DNA strand (which might be a target molecule) and ligated (if they are adjacent), or a DNA polymerase may be used to fill any "gap" between the termini prior to ligation. The regions of the linear precursor, and hence the circular template, which are outside those required for hybridisation to the target can be varied to generate different amplification products. Multiple linear precursors may be directed to different sequences in the target in order to generate multiplex signals. Alternatively, different linear precursors could be directed to the same target sequence in such a way that only perfectly matched sequences would form circular molecules. Such an arrangement might find application in areas such as the detection of different mutations in a common underlying sequence.

Such an overlapping complementary linker strand may act as the primer for the polymerising agent. It may contain (in its final double-stranded form) a cleavage site, meaning that it is only when circularisation has been completed and a double stranded cleavage site produced that cleavage occurs and the polymerising agent is able to bind and produce a complementary strand. For example, the linear strand may have a 3' dideoxyterminus, requiring cleavage to produce a new 3'-deoxy terminus to allow the polymerising agent to work. In particular by placing the primer binding site upstream of the cleavage site, this can prevent cascading polymerising agent activity before the linear nucleic acid sequence has been circularised.

The complementary strand product may be used as a primer for an additional circular template sequence, thereby providing a "cascade" effect—the product of one stage acting as a primer for the next and so on.

The additional circular template sequence may have nucleic acids added/subtracted and/or substituted to it when compared to the first template sequence on any other template sequence.

Thus oligonucleotide synthesis according to the present invention may comprise at least one additional step of providing:

(I) an additional circular nucleic acid template sequence to which will hybridise all or part of said displaced single-stranded linear nucleic acid forming a primer nucleic acid sequence;

(ii) said additional template sequence also having at least one cleavage site which, when rendered double stranded by a complementary strand, provides a cleavage site for a cleavage agent which cleaves only said complementary strand; and (iii) treating said additional sequence and hybridised single-stranded linear nucleic acid with a strand-displacing polymerising agent and the reagents and conditions necessary to effect the action of said polymerising agent, and with said cleavage agent or agents, such that said polymerising agent produces a further complementary strand hybridised to said additional template sequence and which is cleaved at said cleavage site or sites such that it is subsequently displaced as a linear nucleic acid by said polymerising agent.

Linear template strands may also be used in such additional steps. The use of linear template strands is described in more detail below and the synthesis of oligonucleotide products may comprise at least one additional step of providing:

(I) an additional linear nucleic acid template strand to which will hybridise said displaced single-stranded linear nucleic acid forming a primer nucleic acid sequence;

(ii) said additional template strand also having at least one cleavage site which, when rendered double stranded by a complementary strand, provides a cleavage site for a cleavage agent which cleaves only said complementary strand; and (iii) treating said additional template strand and hybridised single-stranded linear nucleic acid with a strand-displacing polymerising agent and the reagents and conditions necessary to effect the action of said polymerising agent, and with said cleavage agent or agents, such that said polymerising agent produces a further complementary strand hybridised to said additional template strand and which is cleaved at said cleavage site or sites such that it is subsequently displaced as a linear nucleic acid by said polymerising agent.

The additional circular nucleic acid template sequence or linear nucleic acid template strand may have a nucleotide or nucleotides added, subtracted and/or substituted to it when compared to the template sequence.

It is known that with existing amplification techniques such as PCR which provide a primer for subsequent extension against a sample template strand that "noise", i.e. false results, can result from unexpected hybridisation and polymerisation. Since the present invention only provides a template strand, the target nucleic acid sequence acting as a primer and being extended, it is possible to prevent such "noise" resulting from the unexpected hybridisation of a linear template strand by ensuring that a linear template strand, even if subject to degradation, cannot be extended. This can be achieved by synthesising it from methyl RNA. Naturally, such problems cannot be encountered with a single circular template sequence, and this avoidance of "noise" can be particularly advantageous.

A single stranded template sequence can be either partially or wholly single stranded. This can be used to allow only those portions of the template to which the primer would bind to be presented as a single strand. This protects the rest of the molecule from non-specific hybridisation, which might otherwise increase unwanted side reactions, or from hybridisation of an amplification product from an identical template which would effectively remove that product from further amplification rounds.

This protection might be provided in a number of ways. For example, a template sequence could have a loop motif downstream of the polymerising agent start site such that, under the conditions of the reaction, it would form a partial hairpin structure with the single stranded primer binding site upstream of this. On binding of the primer, and extension by the polymerase, the double stranded hairpin region would be opened by strand displacement to allow copying of the formerly protected down-stream sequence. In order for these hairpin structures to provide efficient amplification it may be necessary to include, in the loop of the hairpin, nucleotides which are modified such that they cannot serve as template for the polymerase and would terminate extension across the loop. This would prevent synthesis of a product which also contained a hairpin region, which might reform as a double strand in solution, preventing further amplification. Such termination agents might include PNA or inosine residues.

Alternatively, with both circular and linear template sequences, non-primer sequences may be bound to provide double-stranded regions, these sequences subsequently being displaced by the advancing polymerising agent. This may be advantageously used by leaving only primer regions of template strands single-stranded, thereby preventing non-specific hybridisations and subsequent amplification cycles. In the case of linear template strands this would prevent one complementary strand product from hybridising to another identical template strand and effectively removing it from further reactions. Clearly any non-primer sequence hybridised to the template strand should not be extendable by the polymerising agent. Various ways are known of rendering sequences unextendable and include incorporation of a di-deoxyribonucleotide at the 3' end of the molecule. However, all oligonucleotides are subject to some degree of degradation on storage and the use of a single substituted base may not, therefore, be sufficient to maintain protection. More robust protection might be provided by using entirely modified bases such as methyl-RNA oligonucleotides.

The method of the present invention lends itself to the detection of target nucleic acid sequences which may be recalcitrant to amplification by other means (e.g. PCR) and, more particularly, may be used to achieve the optimum reaction conditions for detection of multiple sequences. This may allow the detection of sequences in multiplex reactions which would be difficult or impossible to achieve by other means due to the nature of the sequences to be amplified.

Cleavage agents, and the cleavage sites for which they are specific, are well known—a cleavage site may be a restriction endonuclease site, the template strand (but not the complementary strand) being protected from endonuclease activity by chemical or other modification (e.g. phosphothioate bonds). Restriction enzymes which may be used include BstNI, AvaI, BsmAI BsoBI, BsrI, HincII (New England Biolabs). Alternatively, a cleavage site may be a complementary sequence against which is specific an enzyme which cuts only one specific strand of a DNA duplex. Examples of such enzymes are N.BstSE (Abdurashitou et al., 1996, Mol. Biol. (Mosk), 30(6): 1261–1267) and enzymes not conventionally considered to be restriction enzymes, for example the bacteriophage M13 gpII enzyme which recognises and specifically cuts one strand of a duplex at the f1 origin of replication. Cleavage agents include other than the standard class of proteinaceous enzymes, and include any agent which is capable of catalysing the specific cleavage of a complementary strand and include, for example, RNA ribozymes.

A variety of primer sequences may be used. A polymerising agent will typically be a DNA polymerase enzyme which synthesises a complementary strand in a 5' to 3' direction, adding nucleotides to the 3'-OH terminal of the complementary strand. Thus the 3' end of the primer must be hybridised to the template strand, although the 5' end could, of course, overhang it. In order to be susceptible to the activity of the polymerising agent, the primer must have a free 3'-OH group. This can be provided for example by either a synthetic primer or by having a cleavage site within the double stranded region formed by primer hybridisation with the template strand—upon hybridisation the cleavage agent could act to cleave the primer strand, generating the required 3'-OH group. Alternatively, a cleavage agent such as a restriction enzyme could be used to cleave a double-stranded primer prior to its denaturation and subsequent binding to the template strand. Alternatively, a probe sequence may be hybridised with part of a single stranded primer sequence not possessing a 3'-OH group in a desired position, giving a double-stranded region and a single-stranded region. The single stranded region could then be digested using a single-strand specific nuclease enzyme, leaving a free 3'-OH group, and the primer and probe separated by denaturation, allowing the primer to subsequently hybridise to the template strand.

A wide range of strand-displacing polymerising agents are available and may be used in the methods of the present invention. These include Bca, Bst, Vent, Vent exo⁻; Deep Vent, Deep Vent exo⁻; 9° North, Bacteriophage ø29, Klenow or Klenow exo⁻ (New England Biolabs except Bacteriophage ø29).

As well as simply being used to synthesise oligonucleotide products (e.g. amplify a template strand), the methods of the present invention may also be used for diagnostic purposes—the presence of a specific nucleic acid sequence may be detected by the use of a template strand for which the desired nucleic acid sequence is a specific primer, a sample possibly containing the desired nucleic acid sequence undergoing a detection method according to the present invention, the presence of the desired nucleic acid sequence being determined by detecting the quantity of template sequence complementary strands and correlating the quantity of template sequence complementary strands with the presence of the desired nucleic acid sequence.

Similarly, rather than providing just one template sequence, a range of template sequences may be provided, each being specific for a different primer. In this way, e.g. point mutations in a sequence may be readily detected. In such a case, the template strands could be of different lengths so that their complementary strands could be readily identified by e.g. gel electrophoresis. Alternatively, each template sequence could be provided with a unique marker sequence so that the production of complementary strands could later be determined using e.g. specific probes.

A wide range of methods are known for detecting specific single stranded nucleic acid molecules such as the displaced single stranded nucleic acids (i.e. displaced complementary strands) of the present invention. These may involve capturing the product onto a complementary solid phase oligonucleotide and detecting the structure produced, either by secondary probing or by extending one sequence against the other, including signal generating groups such as biotinylated or fluorescent nucleotides that are then detected. Alternative methods include the use of coupled fluorophore/quencher techniques, such as Molecular Beacons in which the linearisation of a loop structure bearing fluorophore and quenching moieties distances the fluorophore from the quenching moiety, allowing detectable fluorescence.

The methods of the present invention may be used to quantify the presence of any target nucleic acid sequence. The methods of the present invention may be used as diagnostic tests for the presence of a target nucleic acid sequence.

The invention will be further apparent from the following description, with reference to the several figures of the accompanying drawings, which show, by way of example only, forms of detection of target nucleic acid sequences.

Figure 1:
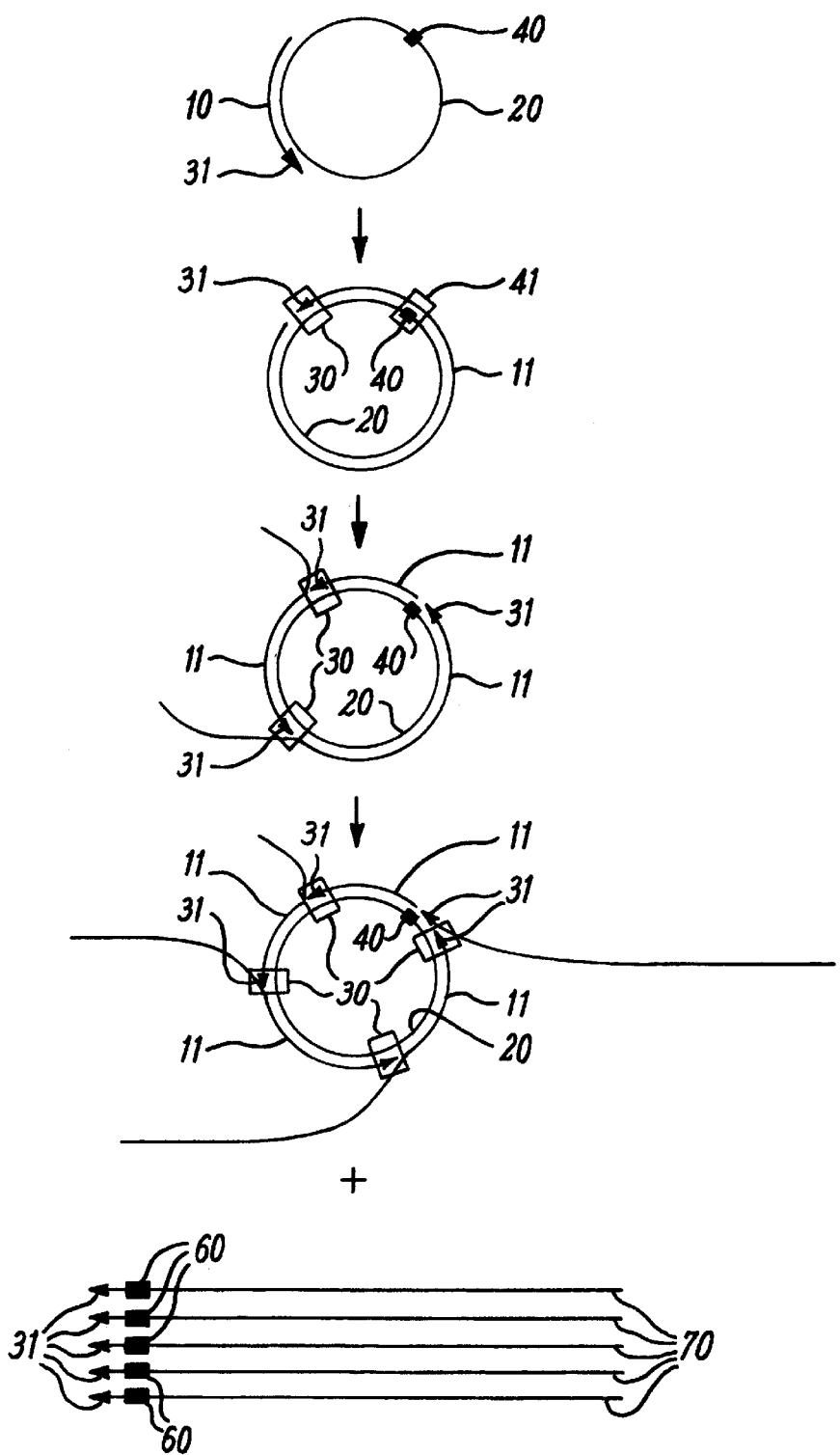
FIG. 1 shows linear amplification of the single strand complement of a circular template.

As can be seen from FIG. 1, the presence of a target nucleic acid sequence 10 in a sample is detected by amplifying a circular template strand 20 by hybridisation of target sequence 10 and using target sequence 10 as a primer. Target sequence 10 is complementary to template strand 20 and upon hybridisation of target sequence 10 to template strand 20, the 3'OH terminus 31 of target sequence 10 is bound by polymerising agent 30 which then proceeds to loop around circular template sequence 20, extending primer 10 to produce fresh complementary sequence 11 and displacing any complementary strand 10, 11 it encounters to give displaced single-stranded complementary strands 70. Template 20 has a cleavage site 40 which, when rendered double stranded by a complementary strand 10, 11 provides a cleavage site for a cleavage agent 41 which nicks only complementary strand 11.

When nicking has occurred, additional polymerising agent 30 is able to bind the exposed 3'OH terminus 31 of strands 10, 11 and extend it to produce additional complementary strand 11. Because strands 10, 11 are cleaved at cleavage site 40 the displaced complementary strands 70 are of finite length and may be subsequently detected as specific size single-stranded extension products (although the exact length of displaced strands 70 may in some cases be foreshortened by an upstream displacing 3' end "catching up"). Displaced single-stranded complimentary strand 70 carries a sequence 60 in a section synthesised as complementary strand 11 to template 20 which was not present in target sequence 10. Sequence 60 is specifically detected by the use of a specific molecular beacon which is used to generate a fluorescent signal proportional to the amount of sequence 60 in the sample and, hence, to the initial amount of target sequence 10 in the sample.

This allows for the possibility of several simultaneously extending 3' ends, giving rise to higher rates of product synthesis than are possible with single uncleavable primers as used in for example RCA.

Since sequence 60 is not present in the starting material, detection of it can be unambiguously attributed to the product of the amplification reaction.

Figure 2:
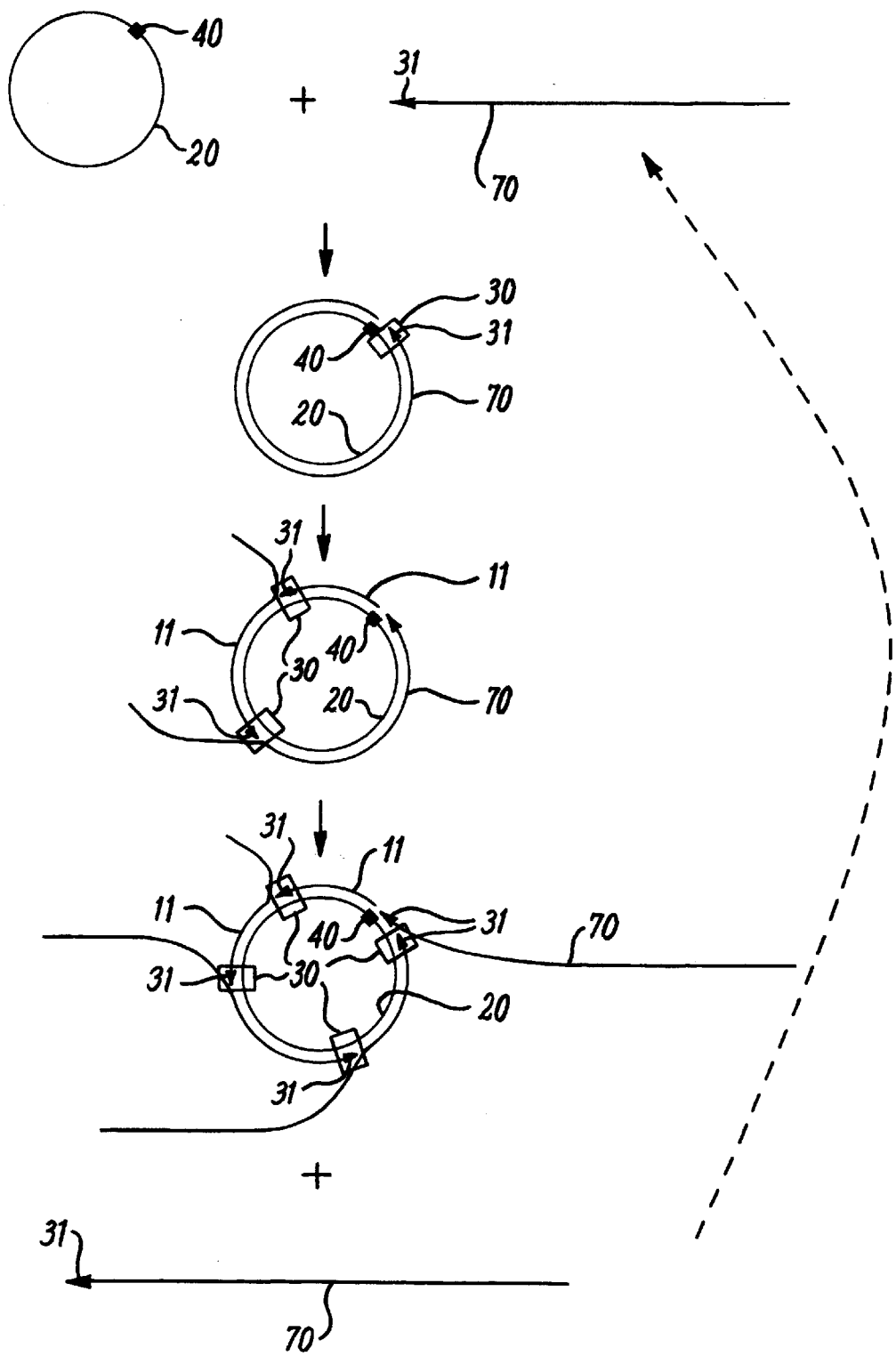
FIG. 2 shows the further processing of the amplified product of FIG. 1 in the presence of a molar excess of closed circular template to which no primer is hybridised.

In the presence of a molar excess of template 20, displaced strand 70 is able to bind other template strands 20 and initiate amplification from them (FIG. 2). Thus a pseudo-exponential amplification is achieved with the rate of product formation being proportional to the initial amount of target 10 and the final amount of product and its rate of synthesis being limited by the quantity of template 20.

Figure 3:
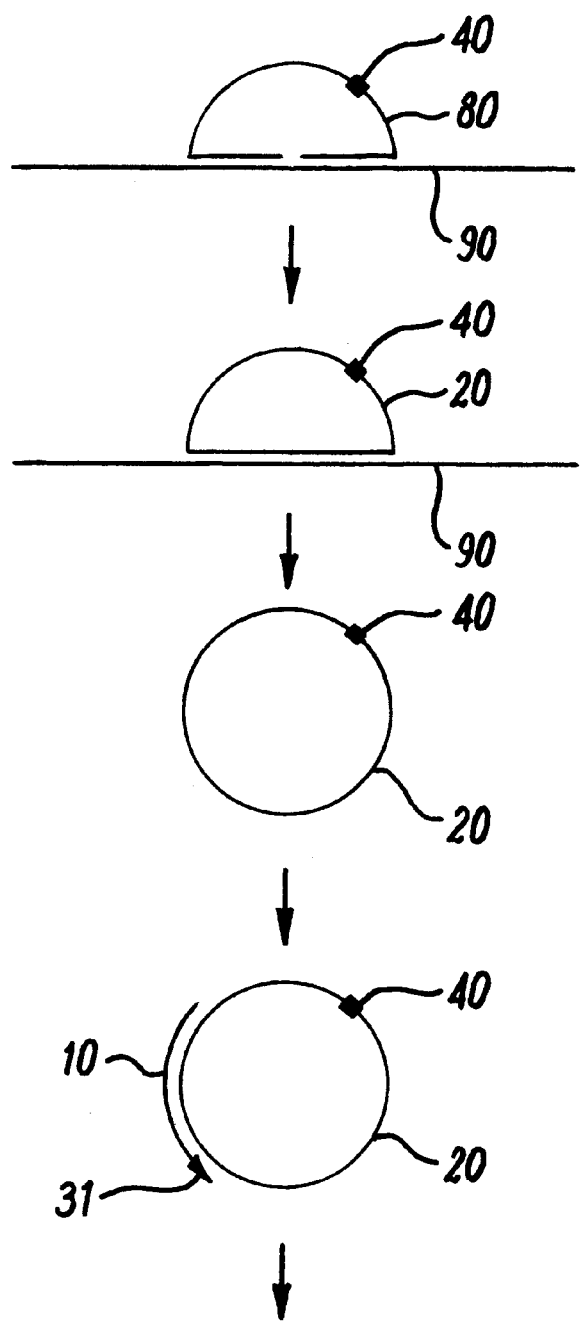
FIG. 3 shows the hybridisation of a linear molecule to a target to generate a circular template for subsequent use.

As can be seen from FIG. 3, a two-stage detection can also be achieved in which a first target strand 90 hybridises both termini of a linear template strand 80. A gap-filling polymerase is used to fill any gap between the termini of linear template strand 80 defined by first target strand 90 with sequence complementary to first target strand 90, and a ligase enzyme is then used to covalently ligate them. This results in the circularisation of linear template strand 80 to form circular template strand 20. Since cleavage site 40 of template strand 20 has not been rendered double-stranded, no cleavage occurs and thus a 3'OH group on the complementary strand is not available for chain extension. Since first target strand 90 is not complementary at its 3' end to template strand 20, 80 it does not hybridise and thus does not provide a basis for chain extension. Thus in order to effect chain extension and amplification an additional target strand 10 is required to hybridise template strand 20, first template strand 90 optionally having been first removed by e.g. melting, in order that the amplification of FIGS. 1 and 2 may proceed. If not removed by e.g. melting then polymerase activity extending additional target strand 10 will cause displacement of first template strand 90.

Figure 4:
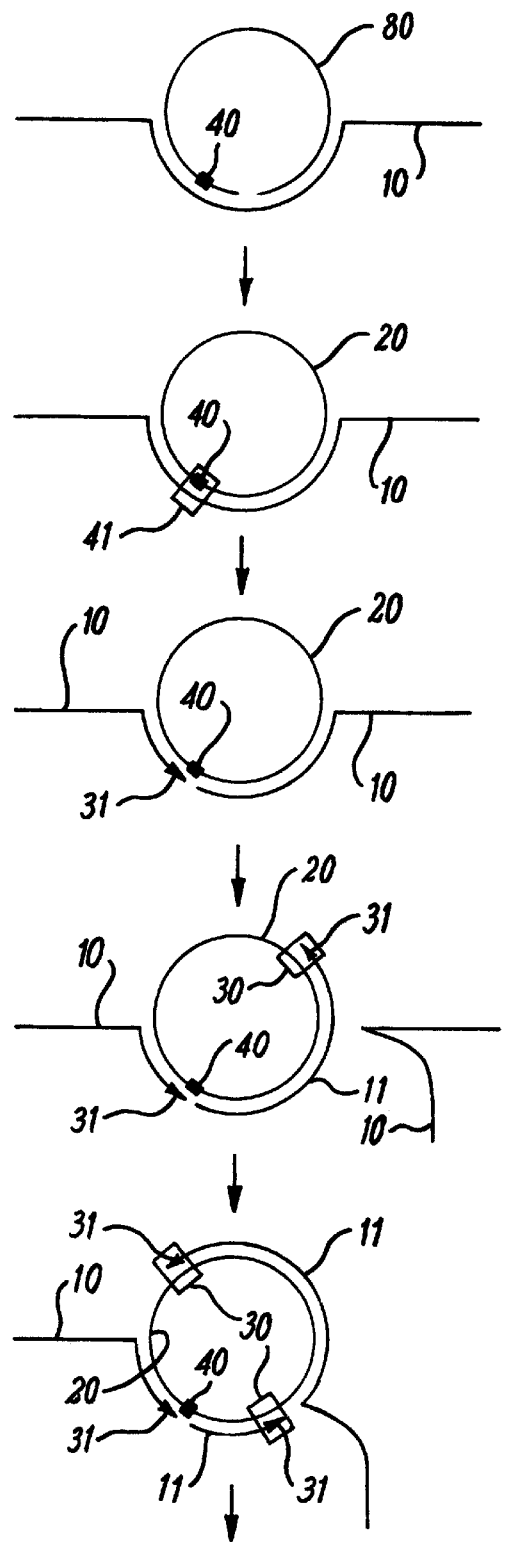
FIG. 4 shows the selection of a suitable target sequence to achieve linear amplification in the absence of additional primers.

FIG. 4 demonstrates how a linear precursor molecule may be circularised, only in the presence of a target, in such a way that linear amplification of the circularised template may be performed in the absence of additional primers. As can be seen, hybridisation of target strand 10 to both termini of template strand 80 results in ligation and circularisation to form circular template strand 20, rendering cleavage site 40 double stranded. Subsequent cleavage and extension allows the displacement of cleaved target strand 10, followed by the displacement of complementary strands 70. This allows confirmation of hybridisation of target strand 10 to both termini of template strand 80. Since the site for the cleavage agent is within the region of hybridisation between target strand 10 and template strand 20, 80 the cleavage agent is able to cleave template 10 to produce a primer sequence which can initiate the amplification process in the absence of exogenously added primer. The reaction will be linear in nature since there is no excess of circular templates. However, the primers produced can be used as initiators of further reactions in order to achieve greater amplification.

Figure 5:
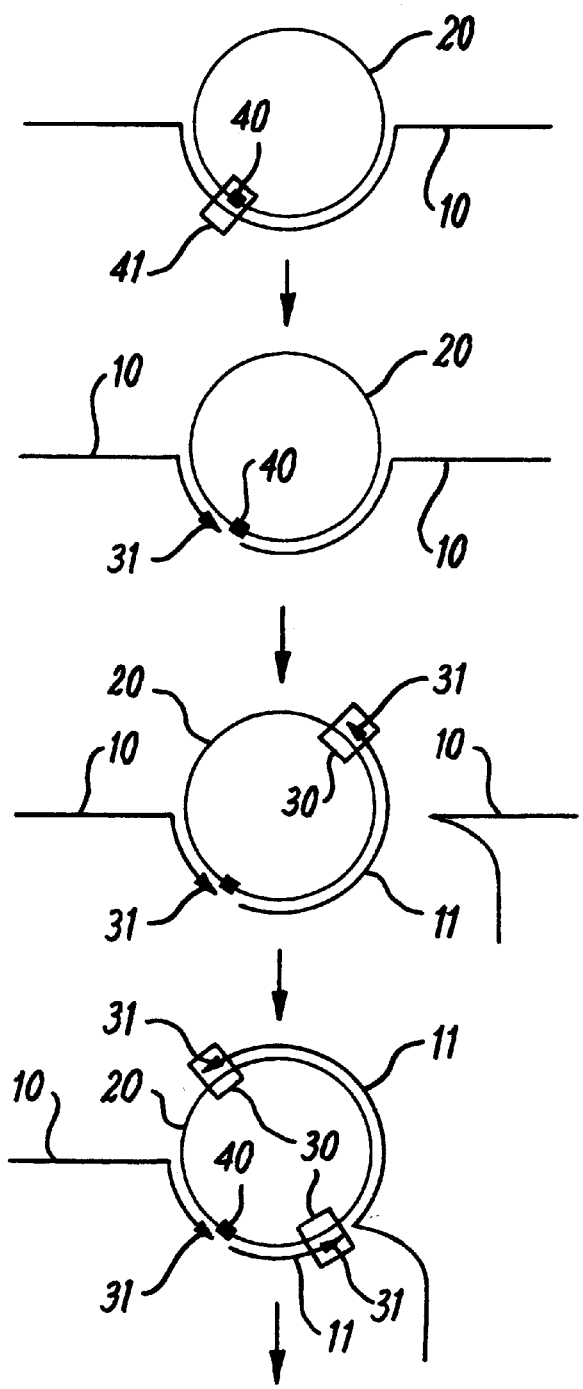
FIG. 5 shows the selection of suitable target sequence to allow the target to initiate an exponential amplification after denaturation.

FIG. 5 illustrates how an exponential reaction may be initiated by providing a molar excess of a circularised template in which the site for action of the cleavage agent is within the region of target hybridisation. Target strand 10 which is only partially complementary to template strand 20 can be hybridised to template strand 20 such that it does not provide a terminal 3'OH group yet does render cleavage site 40 double stranded, cleavage agent 41 subsequently nicking it and providing a 3'OH group 31 for subsequent extension by polymerising agent 30. Repeated extension of target 10, 11 and nicking at cleavage site 40 generates linear products 70 as previously described. In the presence of excess circular template 20, each of these products 70 can hybridise to new template to initiate an amplification reaction, as described, leading to exponential generation of product 70.

Figure 6:
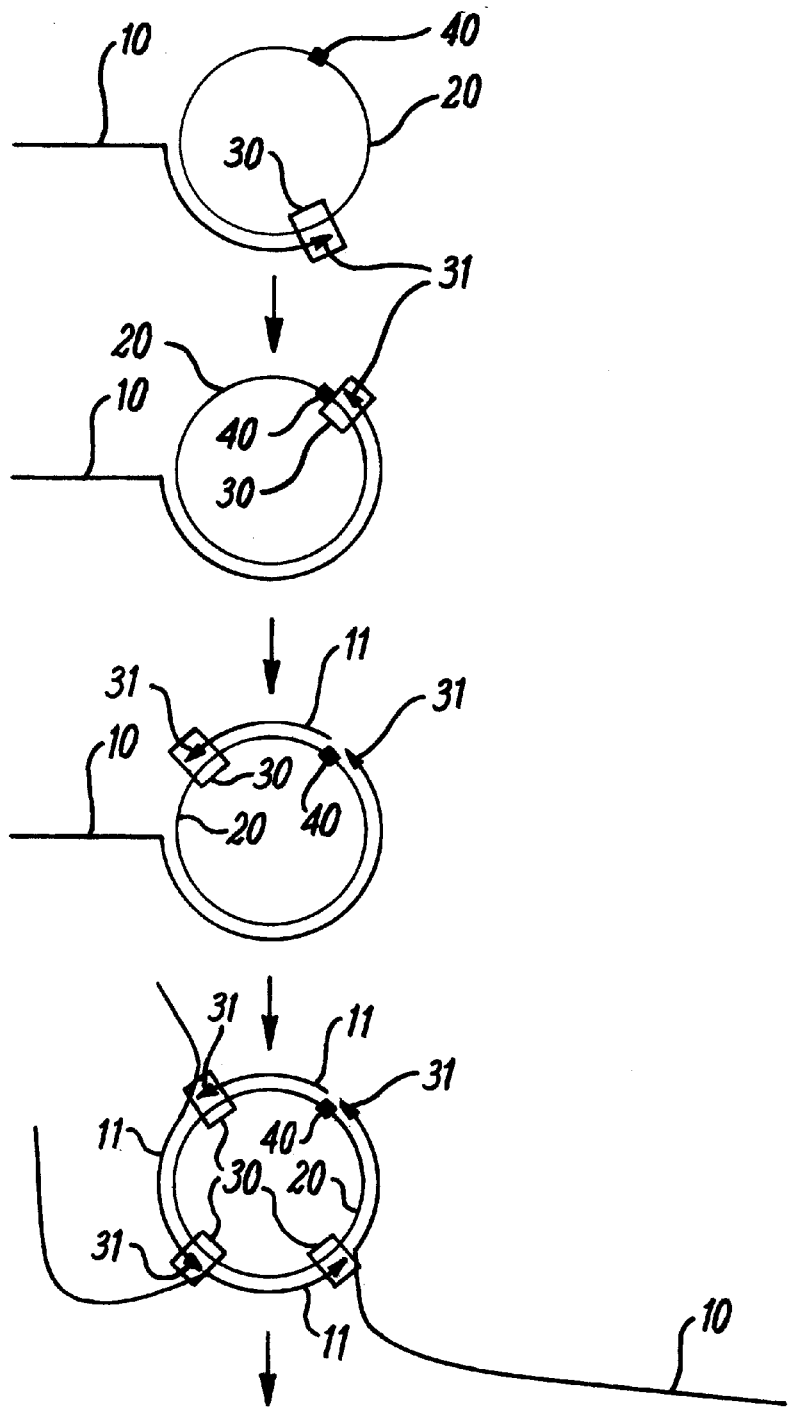
FIG. 6 shows a target initiating an exponential amplification after pre-treatment of same.

FIG. 6 shows a similar exponential amplification (i.e. in the presence of a molar excess of circular template) in which the target has been manipulated such that its 3'OH end, 31, is hybridised to the template 20, and is available for extension by polymerising agent 30. The target strand 10 is only partially complementary to template strand 20 and is hybridised to template strand 20 and provides a terminal 3'OH group for extension by polymerising agent 30, the complementary sequence subsequently synthesised rendering cleavage site 40 double stranded. The terminal 3'OH group 31 is provided by the activity of a restriction enzyme (either an endo- or exo-nuclease) or by random shearing of target sequence 10 or by addition of a probe which will hybridise to target 10 to generate a partially double stranded molecule followed by digestion of the single stranded overhangs by the action of a single strand specific nuclease enzyme.

Figure 7:
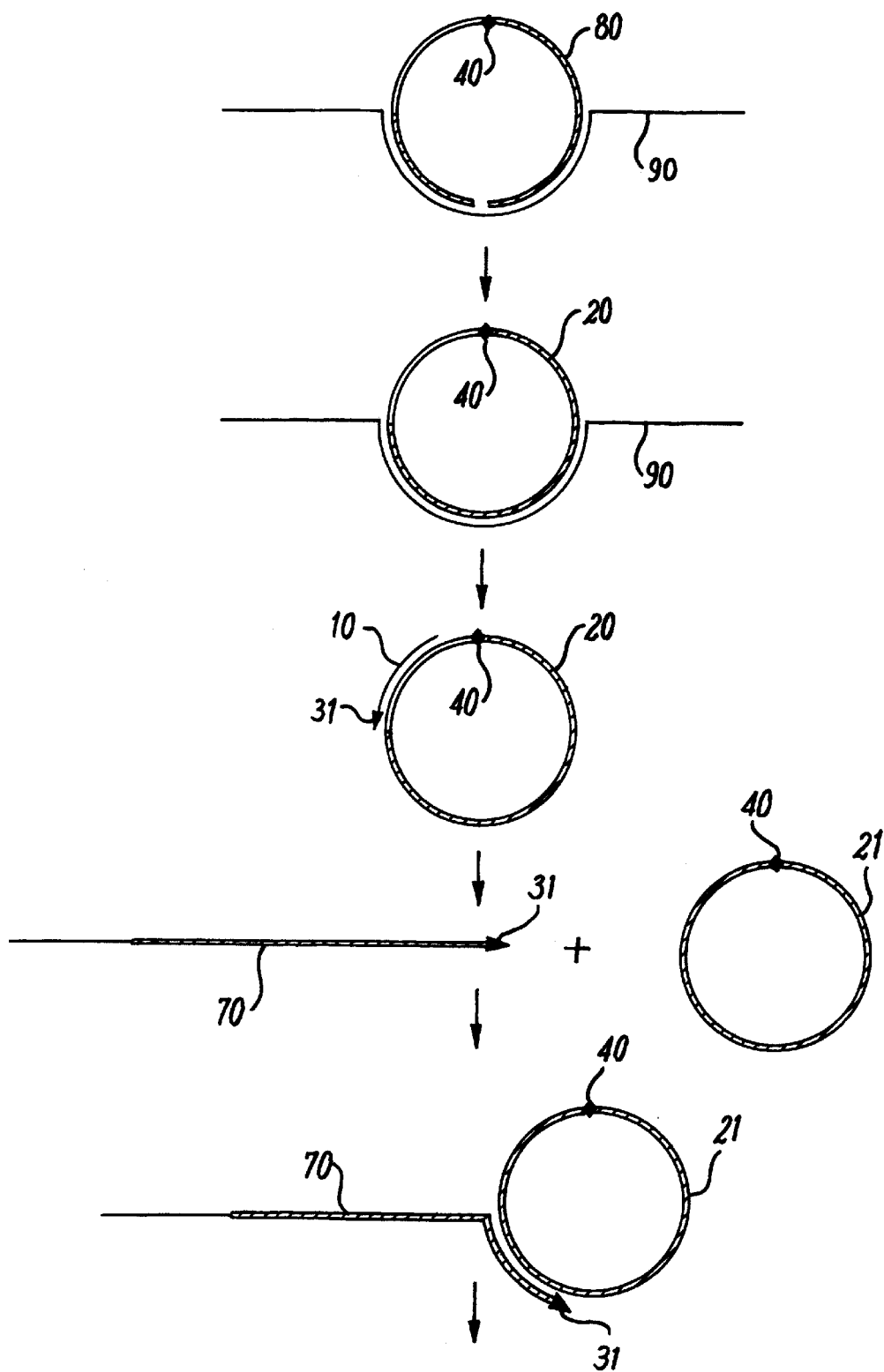
FIG. 7 shows the use of linear and exponential amplification processes to amplify a signal sequence, based upon the presence of a target sequence.

FIG. 7 shows the use of the products of linear amplification (such as those shown in FIGS. 3 and 4) to initiate an exponential reaction by the inclusion of a molar excess of a closed circular template possessing a region of sequence homology with the linear precursor molecule used to generate the linear amplification products (as shown in FIGS. 3 and 4). The region of homology between the two is outside the region of homology with the target sequence and, advantageously, is upstream of the cleavage agent site on the linear precursor fragment. In this position it is impossible for non-specific hybridisation to be extended across the cleavage site to give rise to product which will initiate the exponential reaction. Thus, in FIG. 7, the only region of homology between the linear precursor 80 and the closed circular template 21, shown as dark grey, is such that products of linear amplification 70 of circularised precursor 20, is able to bind in this region to promote exponential amplification in the presence of a molar excess of closed circular template 21.

Figure 8:
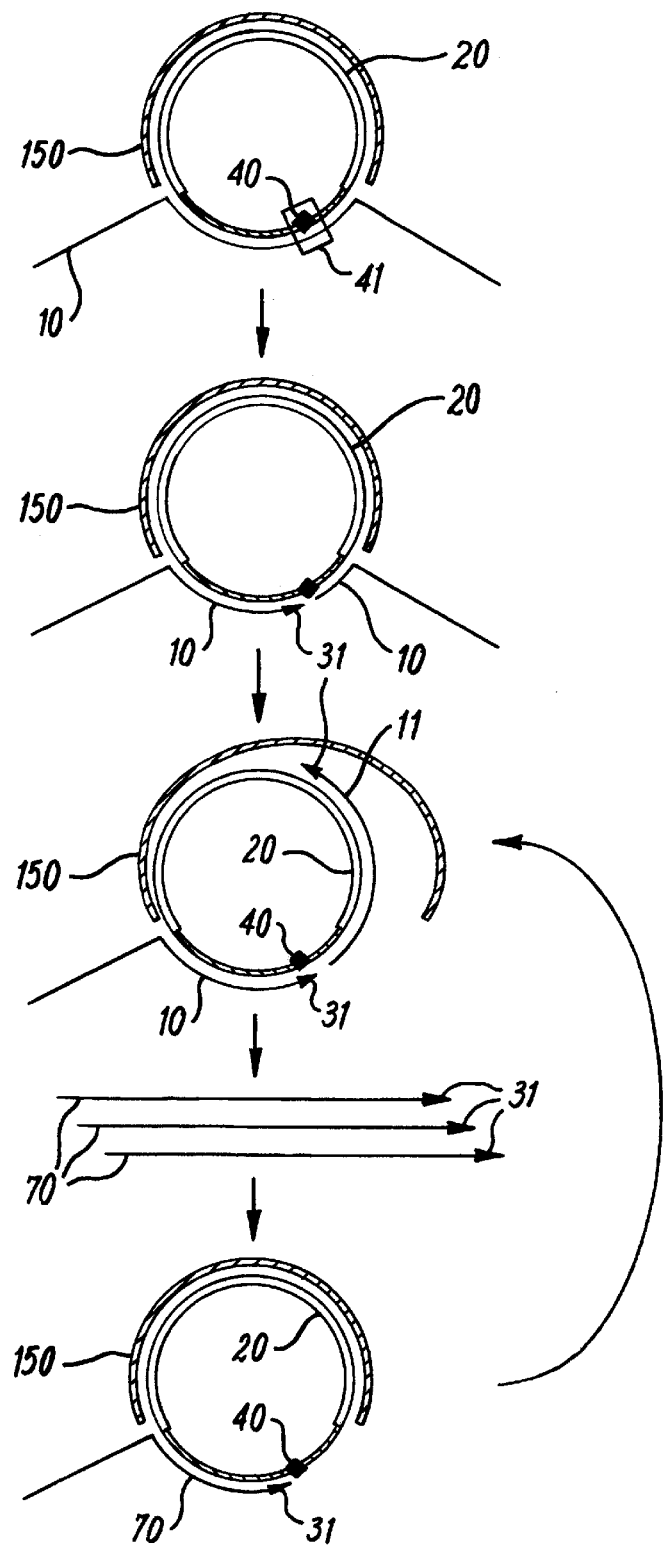
FIG. 8 shows the use of partially double stranded templates to reduce background reactions, which could occur.

FIG. 8 shows the use of a protective complementary strand 150 hybridised to circular template strand 20. Target strand 10 (only partially complementary to a template strand 20) hybridises to a unprotected region of template strand 20 overlapping and rendering double stranded cleavage site 40. Since target strand 1 0 does not provide a terminal 3'OH group, extension cannot occur without the activity of cleavage agent 41, which nicks it and provides a 3'OH group 31 for subsequent extension by polymerising agent 30 to generate complementary strand 11, displacing protective complementary strand 150. Repeated extension of target 10, 11 and nicking at cleavage site 40 generates linear products 70 which can then hybridise to other circular template strands 20, leading to the exponential generation of product 70.

EXPERIMENTAL DATA

The following templates and probes are used.
Templates
TCR001 (linear DNA strand, 37 nucleotides length), 1TCR002 (linear DNA strand, 37 nucleotides length) and TCR003 (circular DNA strand). Nucleotides 17 and 18 of each of TCR001 and TCR002 are joined by a phosphothioate linkage. TCR001 and TCR002 have 3'-T nucleotides comprising propriety blocking agents (Oswel DNA Service, Southampton, UK), which are so modified as to prevent extension from them by the action of DNA polymerase.

Detection Probe (Molecular Beacon)

MOLBEI having the fluorophore FAM (carboxyfluorescien) at the 5' end of the molecule and a quencher moiety (methyl red) at the 3' end.

The probe is designed such that a 6 base-pair region of homology at the ends of the molecule hold it in a hairpin loop formation when in solution. When in the hairpin loop formation the fluorophore and quencher are brought into sufficiently close proximity that fluorescence resonance energy transfer (FRET) dissipates the energy which would otherwise appear as fluorescence. When interacting with a sequence complementary to the internal sequence of the beacon, such as the product of TCR amplification of TCR003 the fluorophore and quencher become separated, preventing FRET and resulting in an increase in fluorescence of the solution.

Target

Specific target: A purified 390bp PCR fragment (CMV390) was generated from human cytomegalovirus DNA. The sequence is part of the GlyB gene and the particular target is a 27 nucleotide sequence within the PCR sequence. This has a naturally occurring site for BstNI (CCIGG) and is used at a final concentration of 2.45 fmol/$\mu$L.

Non-specific DNA

To demonstrate that the amplification reaction is sequence specific non-complementary target is included. This is a collection of DNA fragments constituting the 100 bp DNA ladder (Promega) and is employed at 0.13 mg/$\mu$L.

Reagents 50 mM Magnesium Acetate (MgAc) (SIGMA) Lot No. 77H10581 10×Thermopolymerase buffer (Nex England Biolabs) Lot No. 20 10 mM dNTP (Pharmacia, Polymerisation mix) Lot 7122094021 BstNI restriction enzyme, 10U/$\mu$L (New England Biolabs) Lot No. 10 Bst DNA Polymerase, 8U/$\mu$L (New England Biolabs) Lot No. 13B Molceular Biology Grade (MB) water Equipment Biometra TRIO Thermoblock.

Method

A template mix is prepared, in MB water, containing:

| TCR001 | 100 fmol/$\mu$L |
| TCR002 | 1 pmol/$\mu$L |
| TCR003 | 10 pmol/$\mu$L |

This is used in the preparation of Mix A below:

| Template mix | 10 $\mu$L |
| 10 mM MOLBE1 | 20 $\mu$L |
| 50 mM MgAc | 50 $\mu$L |
| 10 mM dNTP | 5 $\mu$L |
| 10 × Thermo buffer | 25 $\mu$L |
| BSA | 2.5 $\mu$L |
| MB water | 102.5 $\mu$L |

A second mix, Mix B, containing the restriction enzyme and DNA polymerase is also prepared as follows:

| BstNI | 20 $\mu$L |
| Bst Polymerase | 5 $\mu$L |

The following reactions are set up in 0.2 ml flat-topped thin-walled PCR tubes:

| TUBE NUMBER | 1 | 2 | 3 | 4 |
| --- | --- | --- | --- | --- |
| Target (CMV390) | 1.0 $\mu$L | 0 $\mu$L | 0 $\mu$L | 0 $\mu$L |
| Non-specific DNA | 0 $\mu$L | 1.0 $\mu$L | 0 $\mu$L | 0 $\mu$L |
| MixA | 21.5 $\mu$L | 21.5 $\mu$L | 21.5 $\mu$L | 21.5 $\mu$L |
| MB Water | 0 $\mu$L | 0 $\mu$L | 0 $\mu$L | 2.5 $\mu$L |
| MixB* | 2.5 $\mu$L | 2.5 $\mu$L | 2.5 $\mu$L | 0 $\mu$L |
| Total Reaction Volume | 25 $\mu$L | 25 $\mu$L | 25 $\mu$L | 25 $\mu$L |

RESULTS

Under the reaction conditions detailed, enhanced fluorescence can be expected to be observed in Tube 1 in which the TCR amplification reaction has occurred.

What is claimed is:

1. A method for synthesizing oligonucleotide products comprising the steps of:
   providing a circular nucleic acid template sequence having at least one cleavage site which, when rendered double-stranded by a complementary strand, further provides a cleavage site for at least one cleavage agent which cleaves only the complementary strand;
   hybridizing to the template sequence a target nucleic acid sequence to act as a primer nucleic acid sequence;
   treating the template sequence and hybridized primer sequence with at least one strand-displacing polymerizing agent and reagents under conditions necessary to effect the action of the polymerizing agent with the at least one cleavage agent; and
   producing a complementary strand hybridized to the template sequence which is cleaved at the at least one cleavage site with at least one cleavage agent which cleaves only the complementary strand, wherein the complementary strand is subsequently displaced as a single-stranded linear nucleic acid by the polymerizing agent.

2. The method according to claim 1 further including the steps of:
   detecting a displaced single-stranded linear nucleic acid; and
   correlating the results of the detection step with the presence of the target nucleic acid sequence.

3. The method according to claim 2 wherein the primer nucleic acid sequence is hybridized at a position on the template strand distant from the at least one cleavage site.

4. The method according to claim 3 wherein the primer nucleic acid sequence is hybridized at a position on the template strand overlapping the at least one cleavage site.

5. The method according to claim 1 wherein the circular nucleic acid template sequence comprises a circularized linear nucleic acid sequence.

6. The method according to claim 5 wherein the circularized linear nucleic acid sequence is circularized by hybridizing and linking its termini to a complementary linker strand.

7. The method according to claim 1 further including providing an additional circular nucleic acid template sequence to hybridize all or part of the displaced single-stranded linear nucleic acid to form a primer nucleic acid sequence.

8. The method according to claim 7 wherein the additional circular nucleic acid template sequence has at least one cleavage site, when rendered double-stranded by a complementary strand, further provides a cleavage site for at least one cleavage agent which cleaves only the complementary strand.

9. The method according to claim 8 wherein the additional circular nucleic acid template sequence and hybridized single-stranded linear nucleic acid are treated with at least one strand-displacing polymerizing agent and reagents under conditions necessary to effect the action of the polymerizing agent with the at least one cleavage agent such that the polymerizing agent produces a further complementary strand hybridized to the additional circular nucleic acid template sequence and which is cleaved at the at least one cleavage site such that it is subsequently displaced as a linear nucleic acid by the polymerizing agent.

10. The method according to claim 9 further including providing an additional linear nucleic acid template strand to hybridize the displaced single-stranded linear nucleic acid to form a primer nucleic acid sequence.

11. The method according to claim 10 wherein the additional linear nucleic acid template strand has at least one cleavage site, when rendered double-stranded by a complementary strand, further provides a cleavage site for at least one cleavage agent which cleaves only the complementary strand.

12. The method according to claim 11 wherein the additional linear nucleic acid template strand and hybridized single-stranded linear nucleic acid is treated with at least one strand-displacing polymerizing agent and reagents under conditions necessary to effect the action of the polymerizing agent with the at least one cleavage agent such that the polymerizing agent produces a further complementary strand hybridized to the additional linear nucleic acid template strand and which is cleaved at the at least one cleavage site such that it is subsequently displaced as a linear nucleic acid by the polymerizing agent.

\* \* \* \* \*